United States Patent
Koch

(10) Patent No.: US 8,375,942 B2
(45) Date of Patent: Feb. 19, 2013

(54) DEVICE AND PROCESS FOR PROVIDING MOISTENED BREATHING GAS

(75) Inventor: Jochim Koch, Ratzeburg (DE)

(73) Assignee: Dräger Medical GmbH, Lübeck (DE)

(*) Notice: Subject to any disclaimer, the term of this patent is extended or adjusted under 35 U.S.C. 154(b) by 1426 days.

(21) Appl. No.: 11/968,316

(22) Filed: Jan. 2, 2008

(65) Prior Publication Data
US 2008/0190426 A1 Aug. 14, 2008

(30) Foreign Application Priority Data

Feb. 8, 2007 (DE) .................. 10 2007 006 215
Mar. 29, 2007 (DE) .................. 10 2007 015 038

(51) Int. Cl.
*A61M 16/00* (2006.01)
*A61M 16/14* (2006.01)

(52) U.S. Cl. ......... 128/203.16; 128/203.17; 128/203.26; 128/203.27; 128/204.17; 128/204.21

(58) Field of Classification Search ............. 128/203.16, 128/203.12, 203.25, 203.27, 204.17
See application file for complete search history.

(56) References Cited

U.S. PATENT DOCUMENTS 6,102,037 A * 8/2000 Koch ................. 128/203.26
2006/0144395 A1* 7/2006 Koch et al. ........... 128/203.17

FOREIGN PATENT DOCUMENTS

DE 198 08 590 A1 9/1999

* cited by examiner

Primary Examiner — Clinton T Ostrup
(74) Attorney, Agent, or Firm — McGlew and Tuttle, P.C.

(57) ABSTRACT

A respiration moistener (1) has an inlet (3), into which incoming gas (2) to be moistened can be fed. Vapor (21) is mixed with the incoming gas (2) in a mixing chamber (4). Moistened outgoing gas (5) flows out of an outlet (6). In cases in which the temperature of the incoming gas (2) becomes so high that the temperature of the outgoing gas (5) is above a desired value, the internal desired value is adjusted. The outgoing gas (5) can then cool to the desired value on its way through the inspiration tube (7).

6 Claims, 2 Drawing Sheets

DEVICE AND PROCESS FOR PROVIDING MOISTENED BREATHING GAS

CROSS REFERENCE TO RELATED APPLICATIONS

This application claims the benefit of priority under 35 U.S.C. §119 of German Patent Application DE 10 2007 015 038.7 filed Mar. 29, 2007, the entire contents of which are incorporated herein by reference.

FIELD OF THE INVENTION

The present invention pertains to a device for providing moistened breathing gas with a gas inlet, via which moistened incoming gas can be fed, and with a gas outlet for the moistened outgoing gas, as well as with a vapor or moisture feed means, into which a liquid to be evaporated can be fed, and which is provided with an evaporator or an evaporating device, which is controlled by a control device, which sets the outlet temperature and the outlet moisture of the outgoing gas.

The present invention pertains, furthermore, to a process for providing moistened breathing gas.

BACKGROUND OF THE INVENTION

Such a device and such a process are known from DE 198 08 590 A1. The prior-art device is especially a respiration moistener. The prior-art respiration moistener has a breathing gas line with a gas inlet, into which the incoming gas to be moistened can be fed, and a gas outlet, from which the moistened breathing gas is removed. The device has, furthermore, an evaporating device, into which a liquid to be evaporated can be fed. The liquid fed is sent by a dispensing pump to an evaporator, which evaporates the liquid to be evaporated and which feeds the vapor generated into the breathing gas flowing in the breathing gas line. The evaporating device is connected to a control device, which sets the outlet temperature and the outlet moisture of the breathing gas flowing out of the gas outlet. The outlet temperature and the outlet moisture can be regulated independently from each other. The evaporating device may comprise, for example, a dispensing pump, which delivers a quantity of liquid proportional to the volume flow of the breathing gas through the breathing gas line to an evaporating unit. The outlet temperature of the outgoing gas can then be set independently from the fed quantity of liquid by regulating the temperature of the evaporating unit such that the vapor generated by the evaporator reaches a certain temperature and a mixture of breathing gas and vapor, which mixture has the desired outlet temperature, is obtained.

It should however be borne in mind in this context that the temperature of the vapor cannot be below the boiling point of the liquid. In addition, there are hygienic specifications, which require a vapor temperature above the boiling point of the liquid. This may cause the development of an excessively high outlet temperature at the gas outlet of the device when the inlet temperature assumes excessively high values. This may happen, for example, when the breathing gas is fed to the gas inlet of the respiration moistener by means of a fan or another pumping device.

SUMMARY OF THE INVENTION

Based on this state of the art, the basic object of the present invention is to provide a device and a process for providing moistened breathing gas, which make it possible to feed heated breathing gas.

In the device and the process, the outlet temperature to be expected is determined by the control device for a preset desired moisture. In those cases in which the temperature to be expected is above a predetermined desired value for the outlet temperature, the outlet temperature is set to a temperature above the desired temperature. Since the breathing gas must travel over the path through the inspiration tube from the gas outlet of the device to the so-called Y-piece, the increased outlet temperature at the gas outlet is not harmful, because the outgoing gas can cool on the way from the gas outlet to the Y-piece to the extent that the desired temperature is again reached at the Y-piece.

The outlet temperature to be expected is preferably determined on the basis of a measured value for the inlet temperature. Even though it is possible, in principle, to use empirical values for the inlet temperature, the measurement of the inlet temperature represents an additional safety feature, because the inlet temperature may vary as a function of the ambient temperature.

Furthermore, the temperature to be expected is preferably determined as a function of the vapor temperature, which has been set by the control device or determined by means of a temperature sensor. The latter offers the advantage that variations in the vapor temperature can be taken into account.

The determination of a temperature to be expected is based, furthermore, on a minimum allowable vapor temperature. In cases in which the actual vapor temperature is below a minimum allowable vapor temperature, the minimum allowable vapor temperature is therefore used to determine the temperature to be expected. As a result, it is possible to avoid values for the temperature to be expected that are unacceptable based on hygienic specifications.

To ensure that the temperature of the outgoing gas up to the so-called Y-piece reaches the desired value, the temperature of the outgoing gas can be determined at the proximal end of the inspiration tube by means of a temperature sensor.

If the temperature of the outgoing gas at the proximal end of the inspiration tube exceeds the preset desired value, the internal desired value, to which the outlet temperature of the outgoing gas is regulated, can be reduced gradually until the temperature of the outgoing gas at the proximal end of the inspiration tube essentially corresponds to the predetermined desired value of the outgoing gas.

In addition, it is possible to reduce the amount of heat introduced into the outgoing gas by gradually reducing the amount of water introduced into the outgoing gas until the temperature of the outgoing gas at the proximal end of the inspiration tube essentially corresponds to the desired value of the outgoing gas.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiment of the invention is illustrated.

DESCRIPTION OF THE PREFERRED EMBODIMENT

Figure 1:
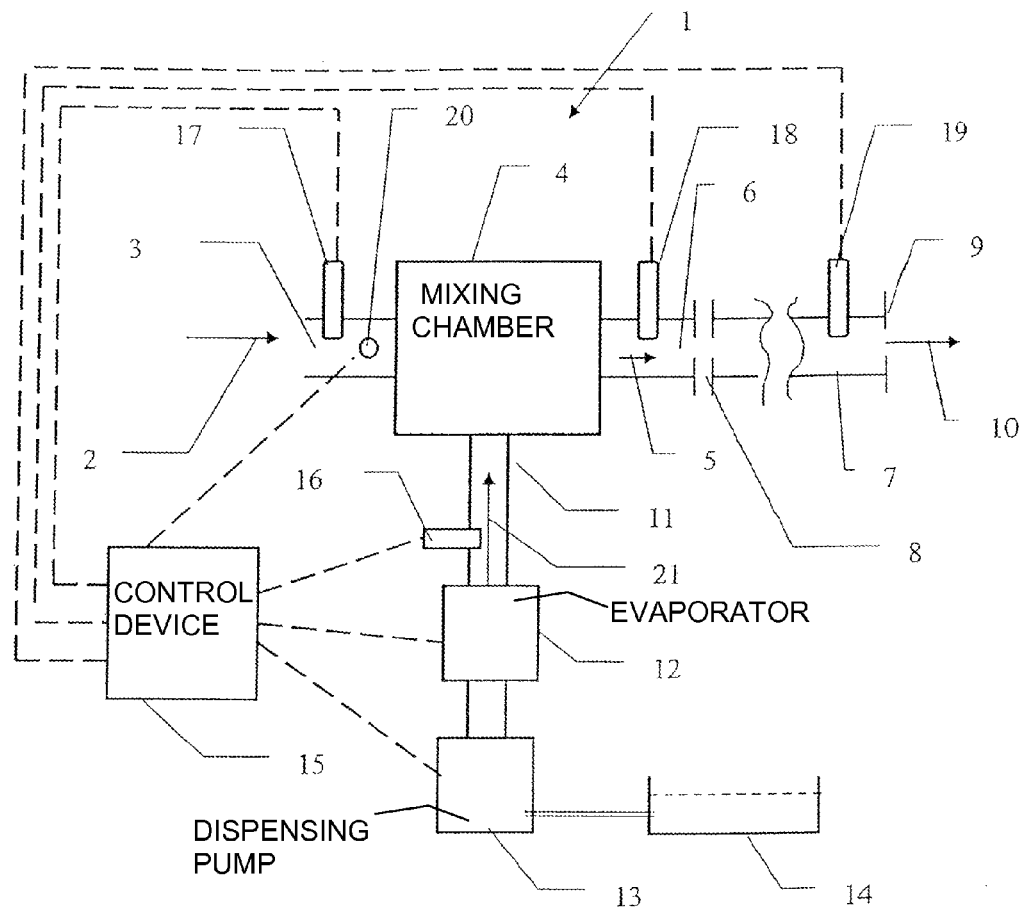
FIG. 1 is a schematic respiration moistener according to the invention, in which the output moisture and the outlet temperature can be controlled either together or separately.

Referring to the drawings in particular, FIG. 1 shows a moistener 1, with which breathing gas 2 flowing in can be moistened. The breathing gas 2 flowing in enters a mixing chamber 4 via a gas inlet 3. Breathing gas 5 flowing out of the mixing chamber 4 enters an inspiration tube 7 via a gas outlet 6. The breathing gas 5 flowing out therefore reaches, via a distal end 8 (spaced a distance from the Y-piece) of the inspiration tube 7, a proximal end 9 (proximate to the Y-piece) of the inspiration tube 7, which tube is connected with its proximal end to a Y-piece, not shown in FIG. 1. Finally, completely processed respiration gas 10 enters the patient's airways via the Y-piece from the proximal end 9 of the inspiration tube 7.

A vapor line 11, which leads to an evaporator 12, is connected to the mixing chamber 4. A dispensing pump 13, which delivers liquid from a liquid reservoir 14 to the evaporator 12, is arranged upstream of the evaporator 12. The liquid is typically water or anesthetic. The dispensing pump 13 and the evaporator 12 are connected to a control device 15. The control device 15 sets the quantity of liquid fed in and the temperature of the vapor such that the breathing gas 5 flowing out has a preset moisture content and a predetermined outlet temperature. Since the inspiration tube 7 is usually heated, the moisture and the temperature of the breathing gas flowing out can be maintained on the way of the gas through the inspiration tube 7, so that the moisture and the temperature of the respiration gas 10 at the proximal end 9 of the inspiration tube 7 are equal to the moisture and the temperature of the breathing gas 5 flowing out.

A vapor temperature sensor 16, which is arranged in the vapor line 11 and is connected to the control device 15, is provided for monitoring the temperature of the vapor generated by the evaporator 12. Another inlet temperature sensor 17, which is arranged in the area of the gas inlet 3, is provided for determining the temperature of the breathing gas 2 flowing in. An outlet temperature sensor 18 arranged in the area of the gas outlet 6 is used to determine the temperature of the breathing gas 5 flowing out. Finally, the temperature of the respiration gas 10 can be determined with a temperature sensor 19, which is located in the area of the proximal end 9 of the inspiration tube 7.

Finally, a flow sensor or flow meter 20 is also provided, which determines the volume flow of the breathing gas flowing in. The flow sensor 20 may likewise be arranged in the area of the gas outlet 6 or at another suitable point in order to determine the volume flow of the breathing gas.

The moistener 1 may be operated according to various control concepts. A first possibility is to control the moisture and the temperature of the breathing gas 5 flowing in separately. The dispensing pump 13 is set in this case by the control device 15 such that a quantity of water proportional to the volume flow of the breathing gas is delivered to the evaporator 12. The heat output of the evaporator 12 is controlled, furthermore, such that the quantity of water fed will be evaporated and that vapor with a vapor temperature is generated in the process and is mixed with the breathing gas 2 flowing in, which leads to an outflowing breathing gas 5 with a predetermined temperature and moisture.

In another control concept, the quantity of water fed to the evaporator per unit of time is changed corresponding to the deviation of the temperature of the breathing gas 5 flowing out from a desired value. This control concept requires that the vapor 21 leaving the evaporator 12 has a constant vapor temperature. This in turn requires that the temperature of the evaporator 12 has a small error and that the vapor 21 leaving the evaporator 12 assumes the temperature of the evaporator 12. Both conditions are usually met in practice. Changes in the temperature of the breathing gas 5 flowing out can be corrected in case of this control concept by changing the quantity of water fed into the evaporator 12 per unit of time.

However, both control concepts reach their limits when the temperature of the breathing gas 2 flowing in assumes such high values that the desired value for the temperature of the breathing gas 5 flowing out cannot be complied with any longer, because the temperature of the water vapor 21 cannot be lowered below the boiling point of water in any case. Moreover, hygienic specifications, which require, for example, that the temperature of the water vapor 21 does not drop below 130° C., must be complied with in practice as well.

Even though it is also possible, in principle, to reduce the quantity of water fed into the evaporator 12 per unit of time and to reduce hereby the quantity of water fed into the breathing gas 2 flowing in, this leads to a reduction of the moisture in the breathing gas 5 flowing in, so that the lung of the patient being respirated may dry out.

Figure 2:
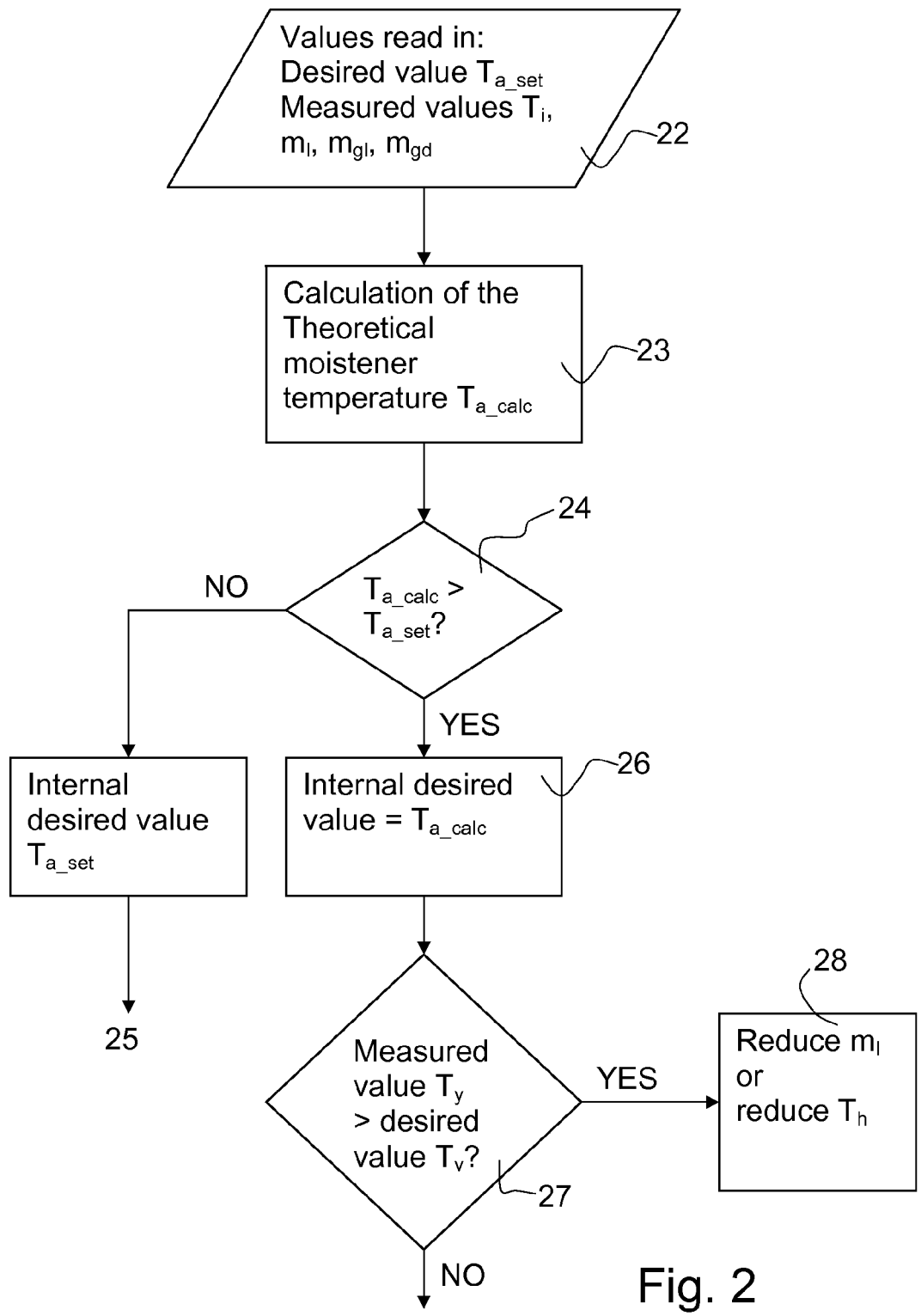
FIG. 2 is a flow chart showing a process according to the invention for controlling the respiration moistener from FIG. 1.

To avoid this risk, the various control concepts are modified according to FIG. 2. FIG. 2 shows the essential process steps of a modified control process, which may be one of the two control processes as desired.

The modification of the control process shown in FIG. 2 begins with a reading-in step 22, in which various parameters are read in unless they had already been read in preceding process steps not shown in FIG. 2. Specifically, the preset desired value $T_{a\_set}$ for the temperature of the breathing gas 5 flowing out is read in. Other parameters to be read in are the weight $m_1$ of the quantity of liquid fed to the evaporator 12, the weight $m_{gd}$ of the dry breathing gas 2 flowing in as well as the weight $m_{gl}$ of the quantity of liquid contained in the breathing gas 2 flowing in the vapor form. These measured variables are likewise determined by suitable measuring sensors. The temperature $T_i$ of the breathing gas 2 flowing in is also read in from the inlet temperature sensor 17. Furthermore, a heating temperature $T_h$ is determined, which is basically equal to the heating temperature that is necessary for the breathing gas 5 flowing out to assume the desired value $T_{a\_set}$, but which is at least equal to the boiling point of the liquid or is the minimum temperature required for hygienic reasons.

A mixing temperature $T_{a\_calc}$ to be expected can be calculated for the breathing gas 5 flowing out on the basis of these parameters:

$$T_{a\_calc} = \frac{m_1 \cdot c_1 \cdot T_h + m_{gd} \cdot c_d \cdot T_i + m_{g1} \cdot c_1 \cdot T_i}{m_1 \cdot c_1 + m_{gd} \cdot c_d + m_{g1} \cdot c_1}$$

in which $c_1$ is the specific heat of the vapor 21 of the liquid and $c_d$ is the specific heat of the dry breathing gas 2 flowing in.

The calculation of the mixing temperature $T_{a\_calc}$ to be expected is based on the circumstance that the enthalpy of the breathing gas 5 flowing out is equal, based on the mixing operation, to the sum of the enthalpy of the breathing gas 2 flowing in and the enthalpy of the vapor 21 fed in.

The calculation step 23 is followed by a branching step 24, in which it is determined whether the outlet temperature $T_{a\_calc}$ to be expected is greater than the desired value $T_{a\_set}$ for the breathing gas 5 flowing out.

If the temperature $T_{a\_calc}$ to be expected is lower than or equal to the preset desired value, the internal desired value is set to the preset desired value $T_{a\_set}$ in an assignment step 25, after which the control process can be continued.

If, by contrast, the temperature $T_{a\_calc}$ to be expected is greater than the preset desired value $T_{a\_set}$, the internal desired value is made equal to the temperature value $T_{a\_calc}$ to be expected in an assignment step 26.

If this is so, the temperature $T_{a\_calc}$ to be expected of the breathing gas 5 flowing out is used as the internal desired value for the control of the temperature of the breathing gas 5 flowing out. The breathing gas 5 flowing out of the gas outlet 6 now has a temperature that is above the preset desired value $T_{a\_set}$. If, by contrast, the outlet temperature $T_{a\_calc}$ to be expected is not greater than the desired value $T_{a\_set}$, the temperature of the breathing gas 5 flowing out, which temperature is determined by the outlet temperature sensor 18, is adjusted to the preset desired value $T_{a\_set}$.

Consequently, the temperature of the breathing gas 5 flowing out may be above the desired value $T_{a\_set}$ if the temperature $T_i$ of the breathing gas 2 flowing in assumes excessively high values. However, the breathing gas 5 flowing out will release heat on its way through the inspiration tube 7 when the heating of the inspiration tube 7 is controlled correspondingly. It is therefore possible that the temperature of the breathing gas 5 flowing out can drop to the desired value $T_{a\_set}$ until it reaches the proximal end 9 of the inspiration tube 7.

Furthermore, to monitor the temperature of the respiration gas 10 at the proximal end 9 of the inspiration tube 7, a respiration temperature $T_y$ of the respiration gas 10 is determined by the temperature sensor 19. A poll is performed in a branching step 27 following the assignment step 26 to determine whether the respiration temperature $T_y$ determined is greater than a desired value $T_y$ set of the respiration temperature. If not, the control process is continued. Otherwise, either the quantity of the liquid fed into the evaporator 12 is reduced or the temperature of the vapor 21 is lowered in a reducing step 28 and the control process is subsequently continued.

It shall be noted that the process steps shown in FIG. 2 can be repeated at periodic intervals.

Regardless of the embodiment of the control process, which is used to control the moisture and the temperature of the outgoing gas, it is advantageous if the inlet temperature $T_i$ of the breathing gas 2 flowing in at the gas inlet 3 is known. In addition, the volume flow should be determined, from which the mass flow can be readily determined if the pressure is known. In addition, the mass flow can also be determined directly by means of a hot wire gas flowmeter or hot film gas flowmeter. In addition, the mass flow of the breathing gas 2 flowing in may be delivered by a respirator. The mass flow of the liquid fed into the evaporator 12 is obtained either on the basis of the delivery capacity of the dispensing pump 13 or from characteristics, which link the temperature of the vapor 21 with the temperature of the breathing gas 5 flowing out assuming a certain inlet temperature $T_i$.

Furthermore, it shall be noted that it is also possible to use an evaporating device with a capillary pump with integrated evaporator and a downstream heating device instead of the dispensing pump 13 and the evaporator 12. The evaporation takes place in the capillary pump in this case. The evaporated quantity of liquid now depends on the evaporation capacity of the capillary pump. The temperature of the vapor can then be brought, if desired, to a preset value by the downstream heating device.

The device being described here and the process being described here offer a number of advantages. The triggering of a needless alarm is avoided by the device and the process because the moistener 1 continues to operate even when the temperature of the breathing gas 5 flowing out is above the desired temperature set. On the other hand, the moistener 1 can also be operated at high ambient temperatures and moistures. In particular, it is possible to feed the breathing gas 2 flowing in by means of a blower. Even if only a limited quantity of moisture can be fed for physical reasons, excessively dry breathing gas is avoided with the device because a sufficient amount of moisture is still fed as long as the temperature of the respiration gas 10 at the proximal end 9 does not exceed permissible limit values.

According to one variant of the present invention, the vapor feed means 11, 12, 13 is designed as a moisture feed means, into which a quantity of liquid that is to be evaporated can be fed and which is provided with an evaporating device, which is controlled by a control device 15, which sets the outlet temperature and the outlet moisture of the outgoing gas 5, the control device 15 determining a temperature of the outgoing gas 5 that is to be expected at a given desired moisture and wherein the control device 15 sets the outlet temperature to a temperature above the desired temperature in cases in which the temperature to be expected is above a desired value. The control device 15 is connected especially to an inlet temperature sensor 17, with which the inlet temperature of the breathing gas 2 flowing in can be determined. The breathing gas flow is optionally determined additionally.

Finally, it shall be pointed out that features and properties which have been described in connection with a certain exemplary embodiment can also be combined with another exemplary embodiment, except when this is ruled out for reasons of compatibility.

Finally, it is also pointed out that the singular includes the plural in the claims and in the specification, except when something else arises from the context. In particular, both the singular and the plural are meant especially when the indefinite article is used.

While a specific embodiment of the invention has been shown and described in detail to illustrate the application of the principles of the invention, it will be understood that the invention may be embodied otherwise without departing from such principles.

Appendix

List of Reference Numbers

| | | | |
|---|---|---|---|
| 1 | Moistener | 16 | Vapor temperature sensor |
| 2 | Breathing gas flowing in | 17 | Inlet temperature sensor |
| 3 | Gas inlet | 18 | Outlet temperature sensor |
| 4 | Mixing chamber | 19 | Temperature sensor |
| 5 | Breathing gas flowing out | 20 | Flow sensor |
| 6 | Gas outlet | 21 | Vapor |
| 7 | Inspiration tube | 22 | Reading-in step |
| 8 | Distal end | 23 | Calculation step |
| 9 | Proximal end | 24 | Branching step |
| 10 | Respiration gas | 25 | Assignment step |
| 11 | Vapor line | 26 | Assignment step |
| 12 | Evaporator | 27 | Branching step |
| 13 | Dispensing pump | 28 | Reducing step |
| 14 | Liquid reservoir | | |
| 15 | Control device | | |

What is claimed is:

1. A respiration device for providing moistened breathing gas, the device comprising:
   a mixing chamber;
   a gas inlet feeding incoming gas that is to be moistened to said mixing chamber;
   a gas outlet supplying moistened outgoing gas from said mixing chamber;
   a moisture feed means including a dispensing pump feeding a quantity of liquid that is to be evaporated to an evaporating device and evaporating the fed liquid in the evaporating device to feed vapor with a vapor temperature to said mixing chamber;

a control device for controlling the quantity of liquid fed to said evaporating device by said dispensing pump and controlling a heat output of said evaporating device such that the quantity of liquid fed will be evaporated and such that the vapor with the vapor temperature is generated at said evaporating device and is fed to said mixing chamber and setting an outlet desired temperature and an outlet moisture level of the outgoing gas, said control device determining a temperature of the outgoing gas that is to be expected at a given desired moisture, and said control device setting an outlet temperature of the outgoing gas to a temperature above the desired temperature when the temperature to be expected of the outgoing gas, at the set moisture level, is above the desired temperature.

2. A respiration device in accordance with claim 1, further comprising an inlet temperature sensor for determining the inlet temperature of the breathing gas flowing in wherein the control device is connected to said inlet temperature sensor.

3. A respiration device in accordance with claim 1, further comprising:

an inspiration tube connected to said gas outlet; and a temperature sensor for determining a breathing gas temperature of respiration gas which flows out of a patient proximal end of said inspiration tube, said control device being connected to said temperature sensor.

4. A respiration device in accordance with claim 3, wherein said control device reduces the temperature of said vapor generated by said evaporating device when said breathing gas temperature determined at the end of said inspiration tube exceeds a predetermined limit value.

5. A respiration device in accordance with claim 4, wherein said control device reduces the quantity of liquid fed to said evaporating device when the breathing gas temperature determined at the end of said inspiration tube exceeds a predetermined limit value.

6. A respiration device in accordance with claim 3, wherein:

said control device receives parameters for operation including the desired temperature of the outgoing gas;

upon said control device determining the temperature of the outgoing gas that is to be expected, at the given desired moisture, is above the desired temperature, the control device sets the desired temperature to the temperature of the outgoing gas that is to be expected;

upon the control device setting the desired temperature to the temperature of the outgoing gas that is to be expected said control device determining if said breathing gas temperature determined at the end of said inspiration tube exceeds a predetermined limit value; and upon the control device determining that the breathing gas temperature at the end of said inspiration tube exceeds a predetermined limit value, the control device reduces one of:

the temperature of said vapor generated by said evaporating device; and the quantity of liquid fed to said evaporating device.

* * * * *